United States Patent [19]
Chao

[11] Patent Number: 5,689,835
[45] Date of Patent: Nov. 25, 1997

[54] SPORTS GOGGLES HAVING AN ATTACHABLE NOSE PAD

[76] Inventor: David Yinkai Chao, 1120 Green Acre Rd., Towson, Md. 21204

[21] Appl. No.: 739,262

[22] Filed: Oct. 29, 1996

[51] Int. Cl.⁶ .................................................. G02C 5/12
[52] U.S. Cl. .................................. 2/446; 351/88; 351/132
[58] Field of Search ............................ 2/446, 445, 439, 2/426; 351/88, 132, 138

[56] References Cited

U.S. PATENT DOCUMENTS

| | | | |
|---|---|---|---|
| 3,345,121 | 10/1967 | DeAngelis | 2/446 X |
| 4,405,214 | 9/1983 | Bolle | 351/88 |
| 4,848,893 | 7/1989 | Grendol | 351/88 X |
| 4,951,322 | 8/1990 | Lin | 351/132 X |

Primary Examiner—Peter Nerbun
Attorney, Agent, or Firm—Charles E. Baxley, Esq.

[57] ABSTRACT

A pair of sports goggles includes a frame for supporting lenses. The frame has a central portion for engaging with a nose of a wearer and includes a groove vertically formed in the upper portion. The groove has an open upper end. A nose pad includes a rib formed in the upper portion for engaging with the groove from the open upper end and includes a flap extended upward from the lower portion for engaging with the bottom portion of the center portion of the frame for allowing the nose pad to be easily and stably attached to the frame and to be easily disengaged from the frame.

3 Claims, 2 Drawing Sheets

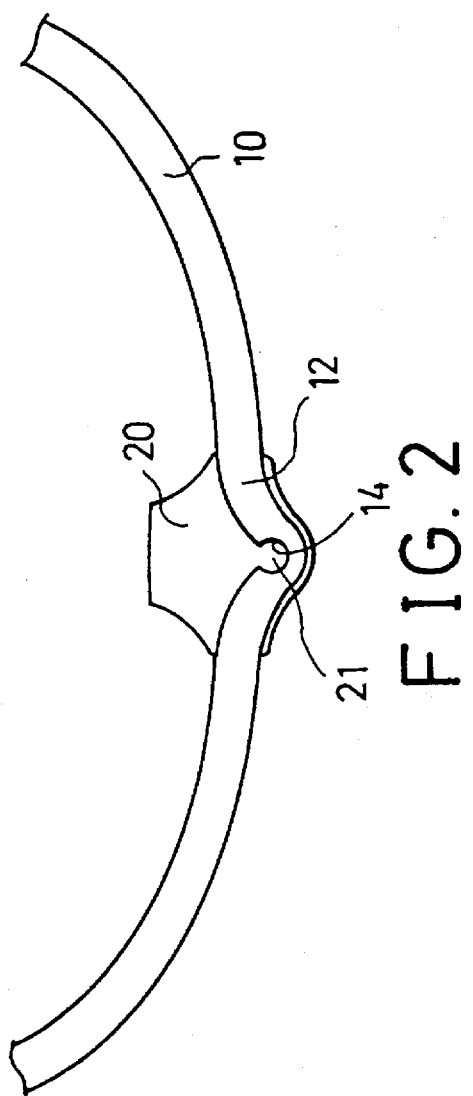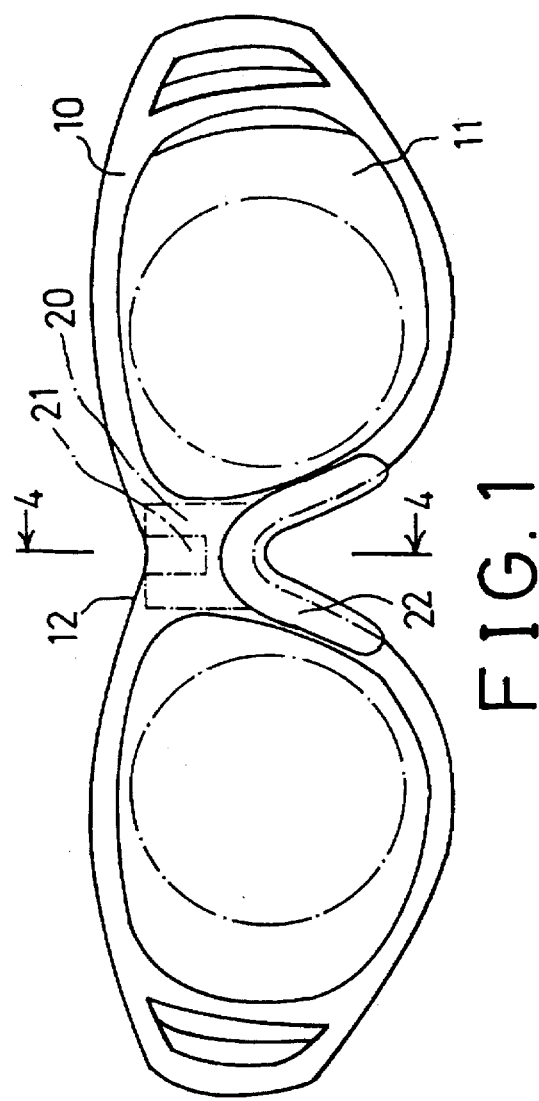

SPORTS GOGGLES HAVING AN ATTACHABLE NOSE PAD

BACKGROUND OF THE INVENTION

1. Field of the Invention

The present invention relates to a nose pad, and more particularly to a nose pad for a pair of sports goggles.

2. Description of the Prior Art

In order to protect the wearer, at least one nose pad is required to be engaged to the sports goggles for preventing the nose of the wearer from being hurt. One typical sports goggles is disclosed in U.S. Pat. No. 4,405,214 to Bolle, and includes a projection for engaging in a groove of the spectacle frame. However, the projection may be easily disengaged from the spectacle frame. The other typical sports goggles is disclosed in U.S. Pat. No. 4,688,272 to Leonardi, and includes a nose pad having an enlarged portion of an elongated member for engaging in an opening of the spectacle frame. However, the nose pad may not be disengaged from the spectacle frame anymore after attached to the spectacle frame. A further typical sports goggles is disclosed in U.S. Pat. No. 5,131,737 to Pernicka, and includes a stretchable body member for engaging on the central portion of the spectacle frame. However, the stretchable body member may become loose after engaging with and disengaging from the spectacle frame for several times.

The present invention has arisen to mitigate and/or obviate the afore-described disadvantages of the conventional sports goggles.

SUMMARY OF THE INVENTION

The primary objective of the present invention is to provide a pair of sports goggles having a nose pad that may be easily attached to and disengaged from the spectacle frame.

In accordance with one aspect of the invention, there is provided a pair of sports goggles comprising a frame for supporting lenses therein, the frame including a central portion for engaging with a nose of a wearer, the center portion of the frame including an upper portion having a groove vertically formed therein, the groove including an open upper end, the center portion of the frame including a bottom portion, and a nose pad including an upper portion having a rib formed thereon for engaging with the groove of the center portion of the frame from the open upper end of the groove, the nose pad including a lower portion having a flap extended upward for defining a channel and for engaging with the bottom portion of the center portion of the frame for allowing the nose pad to be easily and stably attached to the frame and for allowing the nose pad to be easily disengaged from the frame.

Further objectives and advantages of the present invention will become apparent from a careful reading of a detailed description provided hereinbelow, with appropriate reference to accompanying drawings.

BRIEF DESCRIPTION OF THE DRAWINGS

FIG. 1 is a front view of a pair of sports goggles in accordance with the present invention;

FIG. 2 is the top view of the sports goggles;

DETAILED DESCRIPTION OF THE PREFERRED EMBODIMENT

Figure 3:
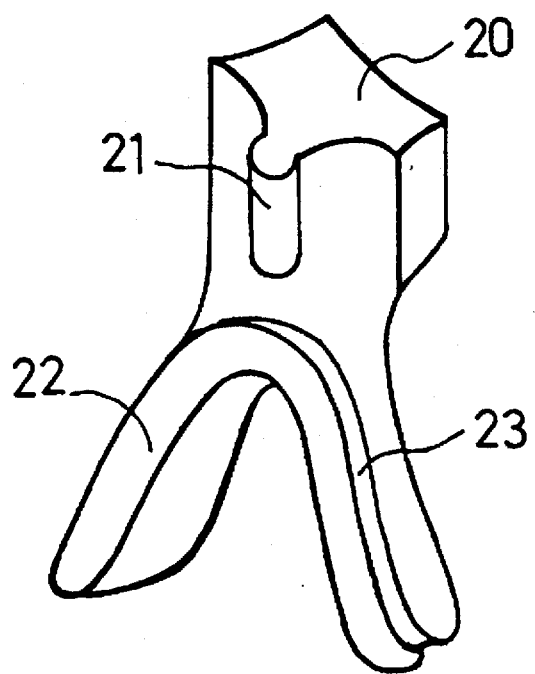
FIG. 3 is a perspective view of a nose pad.
Figure 4:
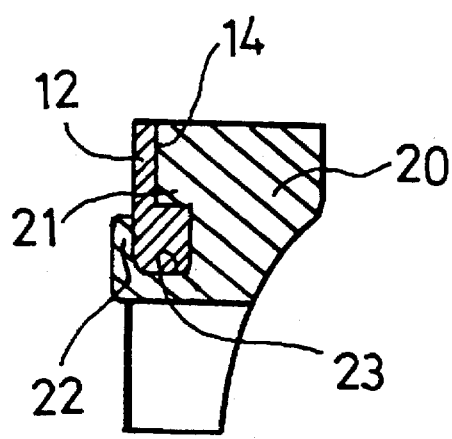
FIG. 4 is a cross sectional view taken along lines 4—4 of FIG. 1.

Referring to the drawings, and initially to FIGS. 1 to 3, a pair of sports goggles in accordance with the present invention comprises a frame 10 for supporting lenses 11 therein. The frame 10 includes a central portion 12 for engaging with the nose of the wearer. The center portion 12 of the frame 10 includes an upper portion having a groove 14 vertically formed therein. The groove 14 includes an open upper end for engaging with a rib 21 of a nose pad 20. The nose pad 20 includes a flap 22 folded or extended upward so as to define a channel 23 for engaging with the bottom portion of the center portion 12 of the frame 10.

It is to be noted that the nose pad 20 is made of resilient material, such as rubber, for engaging with and for protecting the wearer from being hurt. The rib 21 may be easily engaged with the groove 14 of the frame 10 and the flap 22 may be engaged with the bottom portion of the center portion 12 of the frame 10 such that the nose pad 20 may be easily and stably attached to the frame 10 and may be easily disengaged from the frame 10 when required. Accordingly, the nose pad 20 may also be easily replaced and changed with a new one when the previous one is worn out.

Accordingly, the sports goggles in accordance with the present invention includes a nose pad that may be easily and stably attached to the frame and that may be easily disengaged from the frame when required.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A nose pad in combination with a pair of sports goggles, the sports goggles including a frame having a center frame portion for being supported on a nose of a wearer, the frame having an inward side adjacent the wearer and an outward side, the center frame portion having an upper frame portion provided with a vertically formed upwardly opening frame groove, the center frame portion also including a bottom frame portion;

the nose pad including an upper pad portion having a pad rib formed thereon for removable downward engagement into the frame groove;

the nose pad extending on the inward side of the frame from the upper frame portion to a lower pad portion of the bottom frame portion;

the lower pad portion having a flap which is deformable and extends under the bottom frame portion and extends upwardly to the outward side of the frame, the flap defining a pad channel for engaging with the bottom frame portion.

2. The combination as claimed in claim 1 with the nose pad made of a resilient material.

3. The combination as claimed in claim 2 and the frame groove being generally cylindrical, and the pad rib being generally cylindrical.

* * * * *